United States Patent [19]
Petrov et al.

[11] Patent Number: 5,994,536
[45] Date of Patent: Nov. 30, 1999

[54] PROCESS FOR MONO- AND 1,7-BIS-N-β-HYDROXYALKYLATION OF CYCLENE; N-β-HYDROXYALKYL-1,4,7,10-TETRAAZACYCLODODECANE-LITHIUM-SALT COMPLEXES AND THE USE OF THE COMPLEXES FOR THE PRODUCTION OF GADOBUTROL AND ANALOGS

[75] Inventors: Orlin Petrov; Peter Blaszkiewicz, both of Berlin, Germany

[73] Assignee: Schering Aktiengesellschaft, Berlin, Germany

[21] Appl. No.: 09/088,700

[22] Filed: Jun. 2, 1998

[30]   Foreign Application Priority Data

Jun. 2, 1997 [DE] Germany ............... 197 24 186

[51] Int. Cl.⁶ ................................ C07D 487/22
[52] U.S. Cl. ................. 540/474; 540/465; 540/450
[58] Field of Search ................... 540/465, 474

[56]            References Cited
               U.S. PATENT DOCUMENTS 5,064,633  11/1991  Simon et al. ............... 424/1.1
5,277,895   1/1994  Platzek et al. .............. 424/9
5,386,028   1/1995  Tilstam et al. ............. 540/474
5,410,043   4/1995  Platzek et al. ............. 514/184
5,747,000   5/1998  Platzek et al. ........... 424/9.363

OTHER PUBLICATIONS

Tilstam et al., Chem. Abst., vol. 121:57541y., 1994.
Chemical Abstract, vol. 124, No. 25 (Jun. 17, 1996) p. 1324, Abstract No. 343242, 1996, Intrenational Search Report.

*Primary Examiner*—Mukund J. Shah
*Assistant Examiner*—Pavanaram K Sripada
*Attorney, Agent, or Firm*—Millen, White, Zelano, & Branigan, P.C.

[57]              ABSTRACT

The invention relates to the process for mono- and 1,7-bis-N-β-hydroxyalkylation of cyclene, the corresponding mono- and 1,7-bis-N-β-hydroxyalkyl-1,4,7,10-tetraazacyclododecane-Li-salt complexes as intermediate products in the process and the use of the N-(6-hydroxy-2,3-dimethyl-1,3-dioxepan-5-yl)-1,4,7,10-tetraazacyclododecane-LiCl complex for the production of gadobutrol [Gd ocmplex of N-(1-hydroxy-methyl-2,3-dihydroxypropyl)-1,4,7-triscarboxymethyl-1,4,7,10-tetraazacyclododecane].

21 Claims, 2 Drawing Sheets

PROCESS FOR MONO- AND 1,7-BIS-N-β-HYDROXYALKYLATION OF CYCLENE; N-β-HYDROXYALKYL-1,4,7,10-TETRAAZACYCLODODECANE-LITHIUM-SALT COMPLEXES AND THE USE OF THE COMPLEXES FOR THE PRODUCTION OF GADOBUTROL AND ANALOGS

The invention relates to the process for mono- and 1,7-bis-N-β-hydroxyalkylation of cyclene, the corresponding N-β-hydroxyalkyl-1,4,7,10-tetraazacyclododecane-lithium-salt complexes as intermediate products in the process, and the use of the complexes for the production of gadobutrol [Gd complex of N-(1-hydroxy-methyl-2,3-dihydroxypropyl)-1,4,7-triscarboxymethyl-1,4,7,10-tetraazacyclododecane] and analogs.

Mono-substituted and di-substituted N-β-hydroxyalkyl-1,4,7,10-tetraazacyclododecanes are valuable intermediate stages in the production of NMR diagnostic agents (see DE A1 36 25 417, EP 545 511 A2 and EP 0 448 191 A1). The synthesis of these compounds is done by reacting 1,4,7,10-tetraazacyclododecane (cyclene) with epoxides, whereby a mixture of mono-, bis- and tris-alkylated products that is statistical and difficult to separate is produced (WO93/24469). By using a large excess of the expensive polyazamacrocycle, mainly the monoalkylated product can be produced, but the separation from the excess starting material is also a problem, especially in the case of production on an industrial scale (quantities of over 50 kg).

The known methods for the production of N-β-hydroxyalkyl-1,4,7,10-tetraazacyclododecanes requires selective protection of the three nitrogen atoms by reaction with DMF-dimethylacetal, with boranes (H. Bernard et al. Tetrahedron Lett. 1991, 639) or with Cr or Mo-carbonyl complexes (J.-J. Yaouanc et al., Chem. Commun. 1991, 206); these steps are followed by functionalization of the fourth nitrogen atom and subsequent cleavage of the protective group. These methods are very expensive to implement and difficult to use on an industrial scale.

The process for monoalkylation of polyazamacrocycles that is described in U.S. Pat. No. 5,064,633 is limited to the use of α-halocarboxylic acid derivatives and cannot be used for reaction with epoxides for the production of the desired substituted N-β-hydroxyalkyl-1,4,7,10-tetraazacyclododecanes.

The regioselective formylation of monoalkylated cyclene derivatives was described by P. Anelli et al. (J. Chem. Soc., Chem. Commun. 1991, 1317), and the production of 1,7-disubstituted cyclene derivatives by reaction with chloroformic acid esters was described in J. Chem. Soc., Chem. Commun. 1995, 185.

An object of the invention is to provide a process that ensures direct mono- and 1,7-bis-N-β-hydroxyalkylation of cyclene and avoids expensive and multistage protection of the cyclene.

Upon further study of the specification and appended claims, further objects and advantages of this invention will become apparent to those skilled in the art.

Described herein is a process for the production of compounds of general formula I

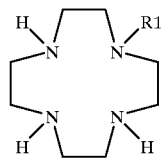

in which
R1 means the group

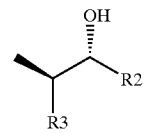

and in which within $R^1$, radicals $R^2$ and $R^3$, independently of one another, in each case stand for a hydrogen atom or together with the carbon atoms to which they are bonded form a 4-, 5-, 6- or 7-membered cycloalkyl ring, which optionally can be interrupted in the ring by 1 to 3 oxygen atom(s), or a $C_1$–$C_{12}$ alkyl radical, which optionally is substituted with 1 to 3 $C_1$–$C_6$ alkyl groups or 1 to 3 hydroxy groups, for example, hydroxymethyl, hydroxyethyl, methyl, ethyl, propyl and butyl, whereby the hydroxy radicals that are present are optionally present in protected form; by reaction of 1,4,7,10-tetraazacyclododecane, optionally in the form of a salt, with an epoxide of formula II,

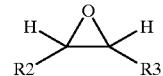

in which $R^2$ and $R^3$ have the above-indicated meanings, in the presence of 0.8–1.1 mol, preferably 0.9–1.0 mol, per mol of the tetraazacyclododecane, of a lithium salt, such as, for example, lithium chloride at temperatures of between 40–150° C., and the reaction mixture that is obtained optionally is worked up by aqueous extraction.

The objects of the invention are further achieved by a process for the production of the compounds of general formula III

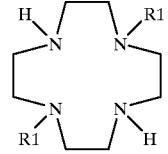

The compounds of general formula (III) can be produced in a way that is similar to that of the compounds of general formula (I), with the difference that more than 1.11 mol, preferably 1.5–3.0 mol, of lithium salt (e.g., lithium chloride) is added, per mol of tetraazacyclododecane. Radicals $R^1$ have the same meaning as the compounds of general formula (I).

By adding different quantities of lithium salt (for example lithium chloride), the selectivity of the alkylation can be controlled. When 1 mol of cyclene is converted in the presence of up to 1.1 mol of lithium salt, the monoalkylated product is selectively obtained, for example, at up to 82% yield with a low proportion of 1,7-disubstituted product. If more than 1.11 mol, preferably 2 and more, of lithium salt per mol of cyclene is used in the reaction, the 1,7-disubstituted product is selectively obtained, for example, at over 80% yield, if more than 2 mol of epoxide of general formula (III) is used. If the quantity of epoxide is increased, for example to 5 to 10 mol per mol of cyclene or higher, the selectivity of the reaction to the 1,7-disubstituted product is preserved.

The following epoxides of general formula II are advantageous for the reaction in the process according to the invention:

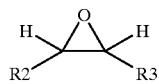

(II)

$R^2$ and $R^3$ have the meaning of hydrogen, methyl, propyl, butyl or higher alkyl, which optionally can be substituted by one or more hydroxyl groups, or $R^2$ and $R^3$ may together with the carbon atoms in the epoxide ring form a 4-, 5-, 6- or 7-membered ring, which can further be interrupted by 1–3 oxygen atoms. Especially advantageous epoxides are cyclopentane-, cyclohexene- and cycloheptene-epoxide, ethylene oxide, propylene oxide, 1,2-butene oxide or 4,4-dimethyl-3,5,8-trioxabicyclo[5,1,0]octane.

The crude products that are thus obtained and that preferably over 80% consist of the desired mono-N-β- and 1,7-bis-N-β-hydroxyalkyl-1,4,7,10-tetraazacyclododecane in the form of lithium complexes can be used directly for the production of NMR contrast media.

As lithium salts, chlorides, bromides, iodides, perchlorates, or trifluoroacetates are preferred. As solvents, dimethylformamide, dimethoxyethane, diethylene glycol-dimethyl ether, toluene or alcohols, such as, e.g., isopropanol or mixtures of these solvents can be used. The process according to the invention is preferably carried out at a temperature of from 40 to 150° C., more preferably in the temperature range of 80–140° C. The reaction time is preferably 20–50 hours.

The invention also includes lithium complexes of the compounds of general formulae (I) and (III). These are obtained by direct crystallization of the reaction product. If the reaction mixture is worked up with the addition of water, the free compounds of general formulae (I) and (III) are obtained.

The entire disclosure of all applications, patents and publications, cited above and below, and of corresponding German application No. 197 24 186.7, filed Jun. 2, 1997 is hereby incorporated by reference.

EXAMPLES

In the foregoing and in the following examples, all temperatures are set forth uncorrected in degrees Celsius; and, unless otherwise indicated, all parts and percentages are by weight.

Example 1

Figure 1:
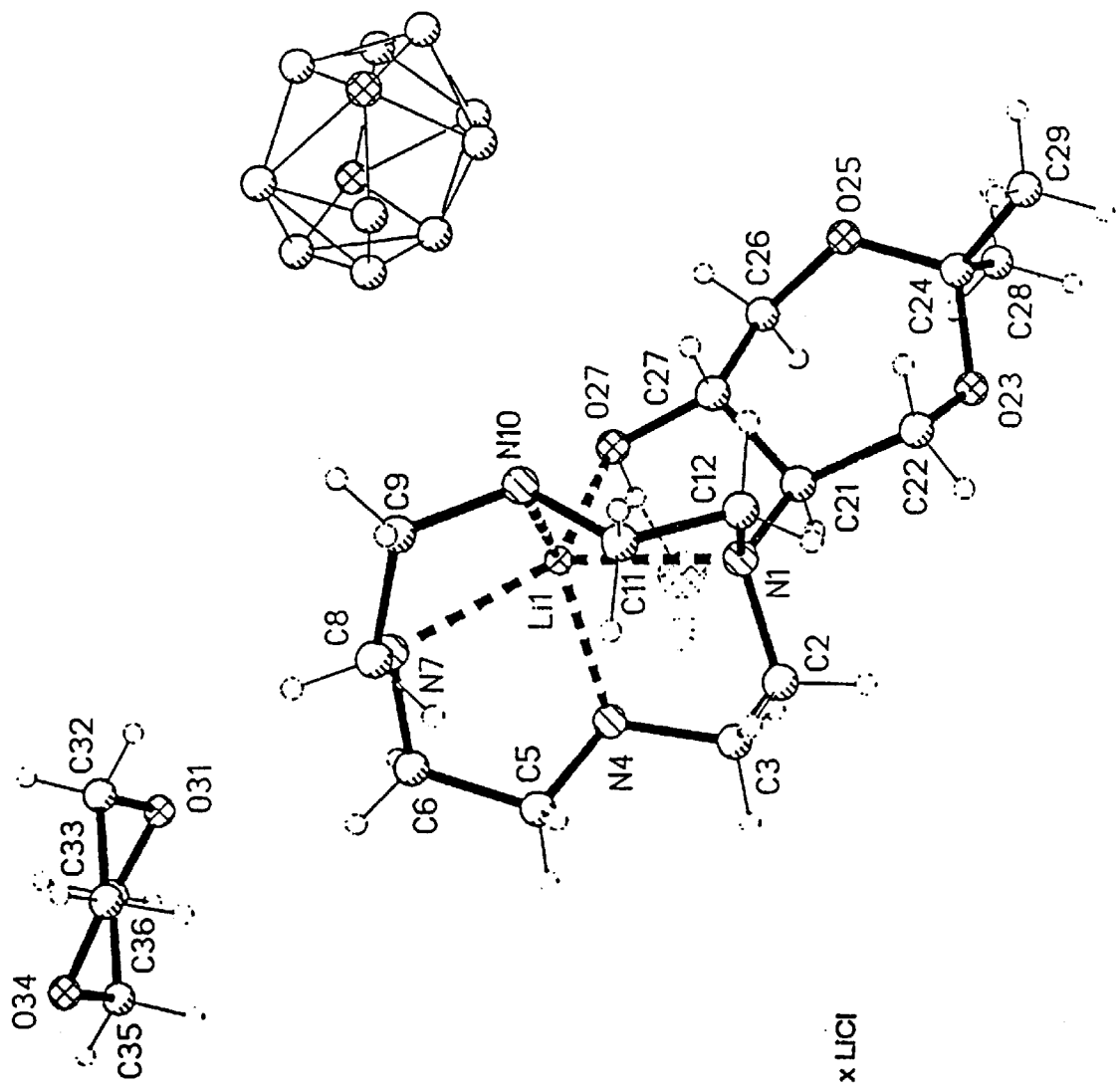
FIG. 1 is the x-ray formulae for Example 1 and FIG. 2 is the x-ray formulae for Example 2.

N-(6-Hydroxy-2,2-dimethyl-1,3-dioxepan-5-yl)-1,4,7,10-tatraazacyclododecane LiCl complex 20 g (116.16 mmol) of 1,4,7,10-tetraazacyclododecane, 4.85 g (116.16 mmol) of LiCl and 19.17 g (133.58 mmol) of 4,4-dimethyl-3,5,8-trioxabicyclo[5,1,0]octane are dissolved in 30 ml of isopropanol and refluxed for 22 hours. Then, the reaction mixture is concentrated by evaporation in a vacuum, and the crude product that is obtained (45.26 g) from 150 ml of MTB-ether is crystallized. 33.9 g (82% of theory) of N-(6-hydroxy-2,2-dimethyl-1,3-dioxepan-5-yl)-1,4,7,10-tetraazacyclododecane.LiCl complex are obtained as white crystals. Melting point 197–199° C. $^1$H-NMR (DMSO-d$_6$): 3.65–3.40 m (5H, CH$_2$—O, CH—O); 2.80–2.35 m (17 H, CH$_2$—N, CH—N), 1.23 s, (6H, CH$_3$). (X-Ray: FIG. 1).

Example 2

1,7-Bis((6-hydroxy-2,2-dimethyl-1,3-dioxepan-5-yl)-1,4,7,10-tetraazacyclododecane LiCl complex 10 g (58.08 mmol) of 1,4,7,10-tetraazacyclododecane, 4.85 g (116.16 mmol) of LiCl and 40.0 g (278.4 mmol) of 4,4-dimethyl- 3,5,8-trioxabicyclo[5,1,0]octane are suspended in 40 ml of isopropanol and refluxed for 60 hours. Then, the reaction mixture is mixed with 30 ml of isopropanol and cooled slowly to 0° C. The crystals that are obtained are suctioned off, washed with 30 ml of methyl-tert-butyl ether and dried in a vacuum. 20.7 g (71% of theory) of 1,7-bis(6-hydroxy-2,2-dimethyl-1,3-dioxepan-5-yl)-1,4,7,10-tetraazacyclododecane LiCl complex is obtained as white crystals.

Figure 2:
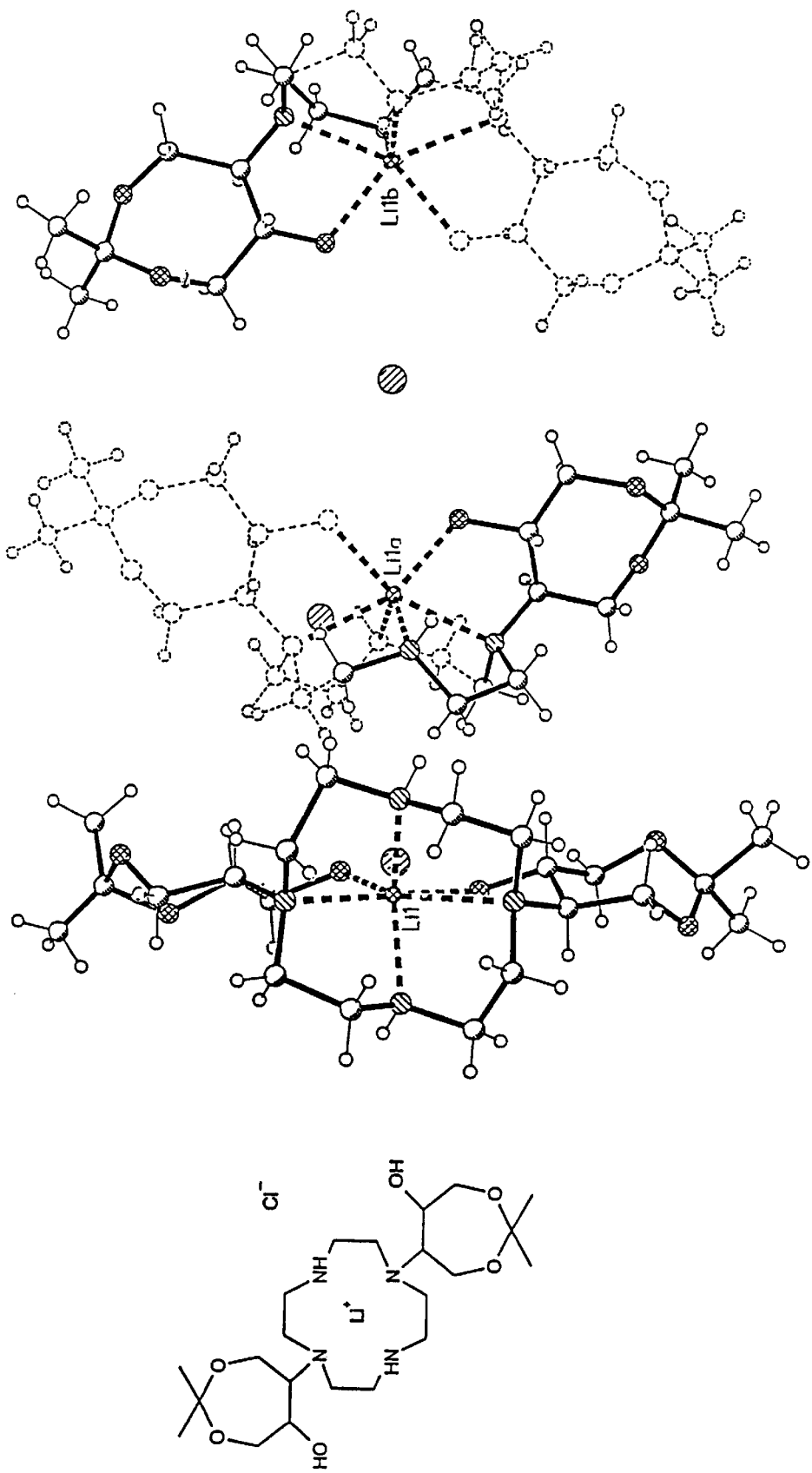

Flash point 262–265° C. $^1$H-NMR (CD$_3$OD): 3.75–3.45 m (10H, CH$_2$—O, CH—O); 2.97–2.30 m (18 H, CH$_2$—N, CH—N), 1.29 s (12H, CH$_3$). X-ray: FIG. 2.

Example 3

N-(6-Hydroxycyclohexyt)-1,4,7,10-tetraazacyclododecane LiCl complex 1 g (5.8 mmol) of 1,4,7,10-tetraazacyclododecane, 0.24 g (5.8 mmol) of LiCl and 0.65 g (6.7 mmol) of cyclohexene oxide (7-oxabicyclo[4.1.0]heptane) are dissolved in 2.5 ml of isopropanol and refluxed for 18 hours. Then, the reaction mixture is concentrated by evaporation in a vacuum. The crude product is crystallized from methyl-tert-butyl ether. 0.95 g (52% of theory) of N-(6-hydroxycyclohexyl)-1,4,7,10-tetraazacyclododecane LiCl complex is obtained as colorless crystals. Melting point 130–135° C. $^1$H-NMR (DMSO-d$_6$): 3.50–3.45 m (1H, CH—O); 2.75–2.30 m (17 H, CH$_2$—N, CH—N), 2.00–1.57 m (4H, CH$_2$—CH$_2$); 1.30–1.08 m (4H, CH$_2$—CH$_2$).

Example 4

1,7-Bis(6-hydroxycyclohexyl)-1,4,7,10-tetraazacyclododecane LiCl complex 10 g (58.08 mmol) of 1,4,7,10-tetraazacyclododecane, 4.85 g (116.16 mmol) of LiCl and 56.5 g (580.0 mmol) of cyclohexene oxide (7-oxabicyclo[4.1.0]heptane) are suspended in 20 ml of isopropanol and refluxed for 20 hours. Then, the reaction mixture is mixed with 30 ml of isopropanol and slowly cooled to 0° C. The crystals that are obtained are suctioned off, washed with 30 ml of methyl-tert-butyl ether and dried in a vacuum. 19.5 g (82% of theory) of 1,7-bis(6-hydroxycyclohexyl)-1,4,7,10-tetraazacyclododecane LiCl complex is obtained as white crystals. Melting point 170–178° C.

$^1$H-NMR (DMSO-d$_6$ 80° C.): 3.48–3.25 m (2H, CH—O); 2.85–2.20 m (18H, CH$_2$—N, CH—N), 2.03–1.50 m (8H, CH$_2$—CH$_2$); 1.30–1.00 m (8H, CH$_2$—CH$_2$). MS (FAB): 369 [M+H]$^+$.

Example 5

Gd Complex of N-(1-hydroxymethyl-2,3-dihydroxypropyl)-1,4,7-triscarboxymethyl-1,4,7,10-tetraazacyclododecane The crude product that is obtained from Example 1 is dissolved in 50 ml of water and mixed at 70° C. with a solution of 38.41 g (406.56 mmol) of chloroacetic acid and 16.26 g (406.56 mmol) of NaOH in 45 ml of water. The reaction mixture is stirred for 6 hours at 65° C., and during this, the pH is kept at 11.0 with NaOH. Then, it is acidified with concentrated HCl to pH 1.5, and the reaction mixture is concentrated by evaporation in a vacuum. The residue is taken up with 500 ml of methanol, and the undissolved salts are filtered off. The filtrate is concentrated by evaporation, dissolved in 500 ml of water, mixed with 18.91 g (52.27 mmol) of gadolinium oxide and stirred for 2 hours at 100° C. Then, it is made neutral with LiOH, and the water is concentrated by evaporation in a vacuum. The residue is crystallized from ethanol/water. 60.92 g of crystalline crude product is obtained. The product is dissolved in 2 l of water and liberated of ionic contaminants by treatment with 500 ml of Amberlite IRA 67 and 500 ml of IRC 50. Then, the solution is concentrated by evaporation, and the residue is recrystallized from EtOH/water.

40.74 g (58% of theory, relative to the feed material) of the Gd complex of N-(1-hydroxy-methyl-2,3-dihydroxypropyl)-1,4,7-triscarboxymethyl-1,4,7,10-tetraazacyclododecane, gadobutrol (DE 42 18 744 A1) is obtained.

Example 6

N-(6-Hydroxycyclohexyl)-1,4,7,10-tetraazacyclododecane)

1 g (5.8 mmol) of 1,4,7,10-tetraazacyclododecane, 0.24 g (5.8 mmol) of LiCl and 0.65 g (6.7 mmol) of cyclohexene oxide (7-oxabicyclo[4.1.0]heptane) are dissolved in 2.5 ml of isopropanol and refluxed for 18 hours. Then, the reaction mixture is concentrated by evaporation in a vacuum. The crude product is taken up in 10 ml of chloroform and extracted with 5 ml of water. The organic phase is concentrated by evaporation. 1.25 g (79% of theory) of N-(6-hydroxycyclohehyl)-1,4,7,10-tetraazacyclododecane is obtained as a colorless oil.

From the foregoing description, one skilled in the art can easily ascertain the essential characteristics of this invention and, without departing from the spirit and scope thereof, can make various changes and modifications of the invention to adapt it to various usages and conditions.

We claim:

1. A process for the production of a compound of formula I

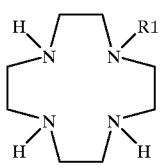

(I)

where R1 is

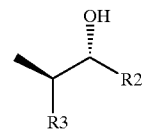

and

R² and R³ are, independently of one another, a hydrogen atom; or together with the carbon atoms to which they are bonded a 4-, 5-, 6- or 7-membered cycloalkyl ring which optionally can be interrupted by 1 to 3 oxygen atom(s); or a $C_1$–$C_{12}$ alkyl radical which optionally is substituted with 1 to 3 $C_1$–$C_6$ alkyl groups or 1 to 3 hydroxy groups, whereby the optionally present hydroxyl radicals are optionally present in protected form, which comprises reacting 1,4,7,10-tetraazacyclododecane, optionally in the form of a salt, with an epoxide of formula II,

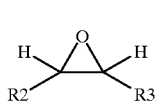

(II)

in which

R² and R³ have the above-indicated meanings, in the presence of 0.8–1.1 mol of lithium salt relative to one mol of cyclene at a temperature of from 40–150° C., and working up the reaction in aqueous form.

2. The process of claim 1, wherein 0.9–1.0 mol of lithium salt is present in the reaction.

3. A process for the production of a compound of formula III

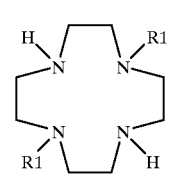

(III)

in which

R¹ is the group

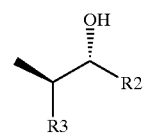

and

R² and R³ are, independently of one another, in each case a hydrogen atom; or together with the carbon atoms to which they are bonded a 4-, 5-, 6- or 7-membered cycloalkyl ring which optionally can be interrupted by 1 to 3 oxygen atom(s); or a $C_1$–$C_{12}$ alkyl radical which optionally is substituted with 1 to 3 $C_1$–$C_6$ alkyl groups or 1 to 3 hydroxy groups, whereby optionally present hydroxy radicals are optionally present in protected form, which comprises reacting 1,4,7,10-tetraazacyclododecane, optionally in the form of a salt, with an epoxide of formula II,

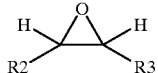
(II)

in which

R² and R³ have the above-indicated meanings, in the presence of more than 1.11 mol of lithium salt relative to 1 mol of cyclene at a temperature of from 40–150° C., and working up the reaction in aqueous form.

4. The process of claim 3, wherein 2.0–3.0 mol of lithium salt is present in the reaction.

5. A lithium complex of a compound of formula I

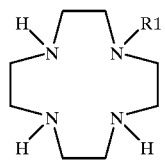
(I)

in which R1 is

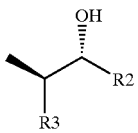

and

R² and R³ are, independently of one another, in each case a hydrogen atom; or together with the carbon atoms to which they are bonded a 4-, 5-, 6- or 7-membered cycloalkyl ring which optionally can be interrupted by 1 to 3 oxygen atom(s); or a $C_1$–$C_{12}$ alkyl radical, which optionally is substituted with 1 to 3 $C_1$–$C_6$ alkyl groups or 1 to 3 hydroxy groups.

6. A lithium complex of a compound of formula III

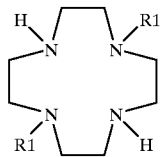
(III)

in which R1 is

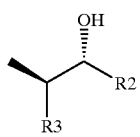

and

R² and R³ are, independently of one another, in each case a hydrogen atom; or together with the carbon atoms to which they are bonded a 4-, 5-, 6- or 7-membered cycloalkyl ring which optionally can be interrupted by 1 to 3 oxygen atom(s); or a $C_1$–$C_{12}$ alkyl radical, which optionally is substituted with 1 to 3 $C_1$–$C_6$ alkyl groups or 1 to 3 hydroxy groups.

7. A complex of claim 6 which is 1,7-bis(6-hydroxycyclohexyl)-1,4,7,10-tetraazacyclododecane LiCl complex, or
1,7-bis((6-hydroxy-2,2-dimethyl-1,3-dioxepan-5-yl)-1,4,7,10-tetraazacyclododecane LiCl complex.

8. A complex of claim 5 which is N-(6-hydroxycyclohexyl)-1,4,7,10-tetraazacyclododecane LiCl complex, or
N-(6-hydroxy-2,2-dimethyl-1,3-dioxepan-5-yl)-1,4,7,10-tetraazacyclododecane LiCl complex.

9. A method for preparing gadobutrol or an analog thereof using a lithium complex of claim 5 as a starting material.

10. A method for preparing gadobutrol or an analog thereof using a lithium complex of claim 6 as a starting material.

11. A method for preparing the Gd complex of N-(1-hydroxy-methyl-2,3-dihydroxypropyl)-1,4,7-triscarboxymethyl-1,4,7,10-tetraazacyclododecane using a N-(6-hydroxy-2,2-dimethyl-1,3-dioxepan-5-yl)-1,4,7,10-tetraazacyclododecane-LiCl complex of claim 5 as a starting material.

12. The process of claim 1, wherein the lithium salt is a lithium chloride, bromide, iodide, perchlorate or trifluoroacetate.

13. The process of claim 1, wherein the lithium salt is lithium chloride.

14. The process of claim 1, wherein the epoxide is cyclopentane-epoxide, cyclohexane-epoxide, cycloheptene-epoxide, ethylene oxide, propylene oxide, 1,2-butene oxide, or 4,4-dimethyl-3,5,8-trioxabicyclo[5,1,0]octane.

15. The process of claim 1, wherein the temperature is from 80–140° C.

16. The process of claim 1, wherein the mono-N-β-substituted compound of formula (I) is selectively obtained with a yield of over 80%.

17. The process of claim 3, wherein the lithium salt is a lithium chloride, bromide, iodide, perchlorate or trifluoroacetate.

18. The process of claim 3, wherein the lithium salt is lithium chloride.

19. The process of claim 3, wherein the epoxide is cyclopentane-epoxide, cyclohexane-epoxide, cycloheptene-epoxide, ethylene oxide, propylene oxide, 1,2-butene oxide, or 4,4-dimethyl-3,5,8-trioxabicyclo[5,1,0]octane.

20. The process of claim 3, wherein the temperature is from 80–140° C.

21. The process of claim 3, wherein the 1,7-disubstituted compound of formula (III) is selectively obtained with a yield of over 80%.

* * * * *